United States Patent [19]

Gieske et al.

[11] 4,183,939
[45] Jan. 15, 1980

[54] GLAUCINE ANALGESIC METHOD

[75] Inventors: Thomas H. Gieske; Philip J. Shea, both of Indianapolis, Ind.

[73] Assignee: The Dow Chemical Company, Midland, Mich.

[21] Appl. No.: 939,144

[22] Filed: Sep. 1, 1978

[51] Int. Cl.² .................... A61K 31/47; A61K 31/485
[52] U.S. Cl. ...................................... 424/258; 424/260
[58] Field of Search ................................. 424/258, 260

[56] References Cited
FOREIGN PATENT DOCUMENTS 866079 4/1978 Belgium .

OTHER PUBLICATIONS

Ishiwata et al., Chem. Pharm. Bull., vol. 18, pp. 1219-1223, 1224-1227, (1970).
Donev, Farmatsiya, (Sofia), 12(4), 17-21, (1962), and 14(2), 49-54, (1964).
Donev, Farmatsiya, (Sofia), 1962, No. 4, p. 17.
Aleshinskaya, Khim. Farm. Zh. 10, (1), 144-147, (1976).

*Primary Examiner*—Stanley J. Friedman

[57] ABSTRACT

A method of alleviating pain in animals comprising administering l-glaucine, d,l-glaucine their pharmaceutically-acceptable salts or mixtures thereof. The levorotary and racemic glaucine compounds have analgesic activity, both orally and parenterally, with a low incidence of side effects.

9 Claims, No Drawings

GLAUCINE ANALGESIC METHOD

BACKGROUND OF THE INVENTION

The present invention concerns the analgesic activity of the l-(levorotary) isomer and the racemate of the alkaloid glaucine, which occurs naturally in the d-(dextrorotary) form. Merck Index, Ninth Ed., Merck & Co., Rahway, N.J. (1976) Monograph 4267.

D-glaucine hydrobromide and d-glaucine hydrobromide are known to have antitussive activity. Donev, Farmatsia (Pharmacy) (Sofia) 1962, No 4, p. 17, and Aleshinskaya, Khim. Farm. Zh. 10, (1), 144–147 (1976) Chem. Abstr. 84:159725 w. In addition, Aleshinskaya, supra, stated that glaucine derived from the yellow horned poppy (d-glaucine), prolongs hexenal and chloral hydrate sleep time in mice, and has analgesic activity at doses of 50–100 mg/kg, as well as adrenolytic activity.

Pharmacological stereospecificity is well known, and there are numerous instances of dramatic differences exhibited by biologically active enantiomers in their interactions with living organisms. Thus, the naturally-occurring levorotary alkaloid, morphine, is a powerful analgesic, while the synthetic dextrorotary enantiomorph is not. One enantiomer, D-(−)-threo-chloramphenicol (the natural product) is a potent antibiotic, while others, such as L-(+)-threo-chloramphenicol, are not. L-(−)-ascorbic acid has antiscorbutic properties, but (+)-ascorbic acid does not; (+)-muscarine has 700 times the muscarinic activity of (−) muscarine; D-(−)-epinephrine is a much more potent vasoconstrictor than D-(+)-epinephrine; and natural (+)-cortisone and (+)-aldosterone are active, racemates have half this activity and the (−) isomers, levorotary isomers, are inactive. Mislow, Introduction to Stereochemistry, W. A. Benjamine, Inc. New York & Amsterdam (1966), p. 137; A. Korolkovas, Essentials of Molecular Pharmacology, Witey Interscience, New York (1970) 97–101, 188–189; Casy, Analgesic Receptors, in A Guide to Molecular Pharmacology-Toxicology, Ed. Featherstone, Marcel Dekker, Inc. New York (1973) Part I, pp 240–246.

Stereospecificity also occurs in synthetic compounds. For example, levo-3-hydroxy-N-methyl isomorphinan is a potent analgesic; the dextro isomer is not (Casy, supra. p. 240) and dextropropoxyphene is a potent analgesic, while levopropoxyphene is not. Merck Index, supra, Monographs 7627 and 5315.

D-glaucine can be isolated from the yellow poppy. The racemate, d,l-glaucine can be synthesized from papaverine, following the procedure of Frank and Tietze, Angewandte Chemie (1967) pp 815–6. A variety of other preparative procedures are also known. Cham and Maitland, J. Org. Chem. J. Chem. Soc. (C) 1966, 753; and Cava, et al. J. Org. Chem. 35, 175 (1970). Separation of the isomers has been carried out by conventional procedures, such as using d,l-tartaric acid to form the d- and l-tartrate salts and separating the salts by fractional cyrstallization.

Glaucine has the structure

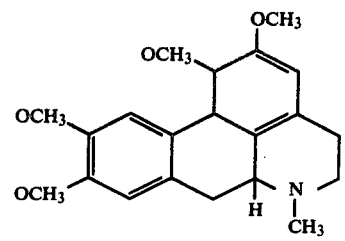

and is thus structurally related to other plant alkaloids such as codeine.

Codeine, and related compounds such as hydrocodone, are well known as narcotic analgesic agents. Merck Index, Ninth Ed., Merck & Co., Rahway, N.J. (1976) monographs Nos. 2420–24 and 4672. Although these compounds are also well known to have a high potential for habituation or addiction, they remain among the most potent and widely used agents.

SUMMARY OF THE INVENTION

This invention is directed to a method of using salts of l-glaucine and d,l-glaucine as analgesic agents.

It has now been found that l- and d,l-glaucine and their pharmaceutically-acceptable salts have analgesic properties and oral absorbtion properties that are unexpectedly superior to those of d-glaucine, and low addictive potential. Certain of the salts, the phosphate and lactate salts, also have unexpected organoleptic characteristics and particularly desirable stability and solubility. As employed herein the phrase "pharmaceutically-acceptable salt" refers to salts of the l- and d,l-glaucines, the anions of which are relatively nontoxic and innocuous to mammals at dosages consistent with good analgesic activity so that side effects ascribable to the anions do not vitiate the beneficial effects of the glaucine.

The glaucine compounds used in the invention can be the levorotary isomer, l-glaucine, or the racemic mixture of levo- and dextrorotary isomers, d,l-glaucine; or a mixture of d- and l-forms containing up to the amount of d-glaucine in the d,l-form. Such mixtures are levorotary, containing more than an equimolar amount of l-glaucine, and thus can be described as mixtures of l-glaucine with the racemic d,l-glaucine. The compounds are preferably employed as pharmaceutically-acceptable salts.

The glaucine salts of the invention are generally crystalline solids which are prepared by reacting l-glaucine or d,l-glaucine (or mixtures thereof) in the form of the base, with a pharmaceutically-acceptable anion under conditions adapted to the formation of salts of organic bases.

The compounds can be readily prepared by reacting the free glaucine base with a pharmaceutically-acceptable acid. The reaction proceeds readily in the presence of an inert organic solvent, such as acetone, ethanol, chloroform methanol, or diethyl ether, or ethyl acetate. The salt typically forms as a precipitate, which can be recovered by conventional techniques such as filtration or decantation and purified by conventional steps such as recrystallization and washing. In some cases, such as the gluconate salt, crystallization is difficult. In such cases, the reaction can be carried out in a non-toxic medium such as water or aqueous alcohol. The resulting salt solution can be used directly, as a solution.

The reaction is typically carried out by dissolving the free base glaucine in the inert organic solvent at a temperature from ambient temperature to the boiling point of the mixture, and adding an equimolar amount or an excess of acid. The acid can be employed, for example, in from about 0.5 to about 1 to 2 to 3 fold molar excess or more.

Mixtures of the pharmaceutically-acceptable salts, and the free base are all useful as analgesic agents, with desirable properties. For convenience it is generally preferred to use a single salt, such as the d,l-glaucine phosphate or l-glaucine lactate or d,l-glaucine hydrobromide, preferred salts being d,l-glaucine hydrobromide, d,l-glaucine phosphate and d,l-glaucine lactate.

The glaucine compounds are highly effective, orally active analgesic agents. Their activity is in some cases combined with surprising palatability and desirable stability and solubility. They also have a useful freedom from undesired side effects, such as addictive properties. They can be administered at dosages of from about 0.1 to about 60 milligrams or more per kilograms (mg/kg) for analgesic use, preferably by oral administration. They are also active parenterally as analgesics, by intraperitoneal or subcutaneous injection, for example.

In practicing the method of the invention, an analgesic amount of one or more of the glaucine compounds in administered internally to an animal, typically a mammal in need thereof, such as a mammal in pain. Administration can be carried out either by a parenteral route, such as by intravenous, intraperitoneal, or intramuscular injection, or by introduction into the gastrointestinal tract via oral or rectal administration, for example.

The analgesic amount of the compound, that is, the amount of the glaucine compound sufficient to alleviate pain symptoms depends on various factors such as the size, type and age of the animal to be treated, the particular compound, salt or mixture of salts and isomers employed, the route and frequency of administration, the severity of pain (if any) and the causative agent involved, and the time of administration. The glaucine salts are generally effective at low dosages when administered orally as compared to parenteral dosages. In particular cases, the dosage to be administered can be ascertained by conventional range finding techniques, for example, by observing the analgesic activity produced at different dosage rates.

Good results can be obtained when the salts are administered orally at dosage rates from about 0.1 to about 0.2, to about 0.5 to about 1 to about 10 to about 20 to 25 to 30 to 40 to about 80 milligrams of glaucine salt compound per kilogram of animal body weight and at rates of 0.1 to 40 mg/kg by intraperitoneal or subcutaneous injection. It is generally desirable to administer individual dosages at the lowest amount which provides the desired suppression of pain symptoms from consonant with a convenient dosing schedule. Oral administration is the route generally preferred.

Dosage units adaptable to oral administration such as tablets, capsules, lozenges, elixirs, syrups and the like are preferred and the active glaucine compound can be formulated in conventional timed release capsule or table formulations.

In using the compounds of the invention, the active glaucine ingredient is preferably incorporated in a composition comprising a pharmaceutical carrier and from about 0.001 to about 95 percent by weight of the glaucine compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use. The compositions can be prepared by known techniques for the preparation of tablets, capsules, lozenges, troches, suppositories, solutions, elixirs, syrups, emulsions, dispersions, wettable and effervescent powders, sterile injectable compositions, and can contain suitable excipients known to be useful in the preparation of the particular type of composition desired.

The compounds may be administered in conjunction with other active ingredients or other analgesic agents. Other active ingredients can include, for example, salicylate analgesics, propoxyphene and caffeine.

Particularly desirable compositions are those prepared in the form of dosage units, such as solid forms, including tablets or capsules containing from about 0.1 milligram to about 20 to 30, to 60 milligrams of the glaucine compound salt per unit.

EXAMPLE 1

A. 3.6 Grams (0.01 mole) of d,l-glaucine base was dissolved in 150 milliliters of Alcohol USP (95 percent ethanol, 5 percent water), with warming to a temperature of 60° C. A solution of 2.0 grams (0.022 mole) of phosphoric acid (88 percent phosphoric acid in water) dispersed in 100 milliliters of Alcohol USP (95 percent ethanol-5 percent water) was added slowly, with stirring, over a period of about twenty minutes. The d,l-glaucine phosphate product began to appear as a precipitate during the phosphoric acid addition. The product was separated by filtration, and found to melt at 240° C. with decomposition. The white crystalline solid product was recrystallized by mixing with 80 percent ethanol in water; heating under reflux and cooling to ambient temperature. The recrystallized product was then taken up and stirred in a mixture of diethyl ether (3 parts) to one part ethanol, separated by filtration, dried and found to melt at 247° C. with decomposition. (Yield 94.3%) C, H, N (calculated) for $C_{21}H_{25}NO_4 \cdot 1\frac{1}{2}H_3PO_4$ 50.3, 5.73, 2.79; found 50.29, 6.03, 2.93.

The elemental analysis is thus consistent with the structure $(d,l$-glaucine$)_2 \cdot 3H_3PO_4$. (The theoretical C, H, N contents calculated for a 1:1 glaucine phosphate $(C_{21}H_{25}NO_4 \cdot H_3PO_4)$ are 55.63, 6.22, and 3.09).

By differential scanning calorimetry the product appears to be at least 95 percent pure, with a single large peak at 247° C., and with about 5 percent or less di-d,l-glaucine phosphate as a single small peak at 227° C. The (d,l-glaucine) phosphate (2:3 salts) crystals are discrete, well-formed white crystals of rod-like to needle-like shape.

B. In a similar procedure 2 grams of l-glaucine hydrobromide was suspended in water, 5 milliliters of aqueous 10 percent sodium hydroxide was added, and the mixture was extracted with two 50 milliliter portions of chloroform. The extracts were dried, filtered and evaporated to dryness. The resulting l-glaucine base was reacted with 0.25 mole phosphoric acid in a procedure similar to that in Example 1C. The crystalline product was separated, dissolved in 5 milliliters of 95 percent ethanol and reprecipitated by addition of diethyl ether, and recrystallized a second time from ethanol. The white crystalline (l-glaucine)$_2 \cdot 3H_3PO_4$-(l-glaucine phosphate) product was found to melt at 242.9° C., with decomposition.

In a similar procedure, the following are prepared:
d,l-glaucine lactate, melting at 153.3° C.
d,l-glaucine acetate, melting at 103° C.
d,l-glaucine pamoate, melting at 198° C.
d,l-glaucine tosylate, melting at 201° C.
d,l-glaucine citrate, melting at 146° C.
d,l-glaucine sulfate, melting at 224° C.
d,l-glaucine maleate, melting at 257° C.
d,l-glaucine salicylate, melting at 199° C.

EXAMPLE 2 l-Glaucine hydrobromide and d-glaucine hydrobromide were evaluated for analgesic activity in protecting mice against characteristic writhing induced by intraperitoneal injection of aqueous 0.1 percent hydrochloric acid, injected 15 minutes after subcutaneous injection of a test compound. In these operations l-glaucine hydrobromide was found active, with an $ED_{50}$ of 5.99 mg/kg (95 percent confidence limits 2.43–14.8) and d-glaucine hydrobromide was found active with an $ED_{50}$ of 12.9 mg/kg (95 percent confidence limits 5.24–31.8).

EXAMPLE 3

In the classical hot plate analgesia test in mice, l-glaucine·HBr was found to have an $ED_{50}$ of 12.7 mg/kg and d-glaucine·HBr and $ED_{50}$ of 23.79 mg/kg. The test compounds were administered by subcutaneous injection 30 minutes before testing.

In a repeated evaluation, with morphine sulfate included for comparison, the $ED_{50}$'s of l-glaucine·HBr, d-glaucine·HBr, and morphine sulfate were determined to be 22.4, 16.0 and 6.3 mg/kg, respectively.

EXAMPLE 4

In the classical tail pinch test for narcotic analgesics, various test compounds were administered by intraperitoneal injection 45–60 minutes before testing. d-Propoxyphene·HCl, codeine phosphate and morphine sulfate were all active with $ED_{50}$'s of 16.7, 6.8 and 1.2 mg/kg. No analgesic activity was observed with d-glaucine·HBr or l-glaucine HBr, indicating a lack of significant morphine-like analgesic activity.

EXAMPLE 5

Test compounds were evaluated for oral analgesic activity in the phenyl-p-quinone mouse writhing test of Hendershot & Forsaith, J. Pharmacol. Exptl. Therap. 125(3), 237 (1959). Test compounds were administered orally 30 minutes prior to the phenyl-p-quinone challenge. The these operations the oral $ED_{50}$'s for l-glaucine·HBr, d-glaucine-HBr and codeine phosphate were determined to be 17.0, 34.0 and 21.1 mg/kg, respectively. In similar operations the oral $ED_{50}$'s for d,l-glaucine phosphate (2:3 salt) and d,l-glaucine lactate were found to be 23.0 and 25.5 mg/kg.

EXAMPLE 6

Test compounds were administered to guinea pigs, and blood samples were collected at 15 minute intervals and analyzed to determine plasma concentration levels of glaucine. In such operations, l-glaucine hydrobromide administered orally at a dose of 5 mg/kg, was found to produce a plasma glaucine level of about 40 nanograms/ml after 15 minutes, increasing steadily to a peak of over 350 nanograms/ml one hour after administration, and remaining about 200 nanograms/ml at the end of the 90 minutes test period. d-Glaucine hydrobromide produced an initial peak plasma level of about 50 nanograms/ml 15 minutes after dosing, which declined to 20–40 nanograms/ml and remained in that range throughout the 90 minute period.

Similar results were obtained with d- and l-glaucine phosphate, with l-glaucine phosphate producing from 3 to 6 or more times the levels obtained with the d-isomer throughout a 120 minute period.

EXAMPLE 7

The abuse potential of d,l-glaucine phosphate was studied in two monkeys in a procedure similar to that described by Deneau, et al., Psychopharmacologia 16(1):30–48, 1969.

In this procedure, the test monkeys are restrained and catheter inserted into the external jugular vein for injection of test substances in response to pressing a bar lever by the monkey. The test monkeys are first habituated to self-administer codeine at a rate of 100 micrograms/kilograms per injection. The self-administration rate of the two monkeys so trained and habituated was about 100 to 150 lever pushes per two hour session at the 100 microgram codeine level. When d,l-glaucine phosphate (2:3) was substituted for codeine, the monkey response rate was found to delcline, from 100–150 responses/two hour session for codeine to 10–20 per two hour session after substitution of d,l-glaucine phosphate, at rates of 50, 100, 200 and 400 micrograms per kilogram injection.

EXAMPLE 8

Physical dependency liability was evaluated in mice by the procedure of Saelens, et al., Aoch. Int. Pharmacodynam, 190:213–218, 1971. In this procedure, mice are administered increasing doses of a test compound at intervals on two consectuive days. The last dosage on the second day is followed by intraperitoneal injection of the morphine antagonist, naloxone, at a dosage of 100 mg/kg, and the mice are observed for characteristic jumping behavior indicative of opiate withdrawals or morphine antaganism. In these operations, morphine sulfate produced stimulation and Straub tail in mice, followed by jumping in 5 of 9 mice (96 jumps total) after naloxone treatment. Codeine phosphate produced Straub tail and stimulation, and naloxone induced jumping in 2 of 6 mice (23 jumps total). d,l-Glaucine phosphate 1:1½ salt as in Example 1 produced no Straub tail at the highest dose (100 mg/kg) and no jumping behavior in any of the eight mice tested. d,l-Glaucine lactate gave results similar to the phosphate, with no jumping in any of the ten mice tested.

EXAMPLE 9

Several d,l-glaucine salts were prepared as 0.2 percent (weight by volume) solutions in distilled water. The various salt solutions were evaluated for palatability by touching a few drops to the tounge. In these operations, which included blind sampling by a trained flavor formulator experienced in flavoring of formulations containing agents such as codeine and dextromethorphan, the hydrobromide was characterized as objectionable with a bitter, sharp and metallic initial taste which increased with time. The sulfate, maleate, citrate, acetate, pamoate and p-toluenesulfonate salts were similar to the hydrobromide and similarly objectionable. The salicylate and succinate salts were ranked as more objectionable than the hydrobromide. d,l-Glaucine phosphate (2:3) and d,l-glaucine lactate were found to lack the sharp, metallic flavor and to be unobjectionable.

EXAMPLE 10

A. Tablets are prepared as follows: 40 grams l-glaucine hydrobromide; 150 grams of modified starch (Sta-Rex 1500) are mixed and granulated with sufficient aqueous alcohol (75 percent water, 25 percent ethanol) to prepare a granulation. The granulation is dried and mixed with 15 grams starch USP; 1.5 grams stearic acid (40 mesh); 0.5 grams hydrogenated vegetable oil (40 mesh) 3 grams colloidal silicon dioxide and microcrystalline cellulose g.s. to 300 grams. The ingredients are mixed and compressed into 300 milligram tablets using 11/32 inch tablet dies. The tablets contain 40 milligrams of l-glaucine hydrobromide each.

B. Capsules are prepared by blending 10 grams d,l-glaucine hydrobromide 3 grams colloidal silica; 2 grams stearic acid and 285 grams lactose; and filling the blend into No. 2 gelatin capsules, 300 milligrams per capsule. This provides 10 milligrams of the glaucine salt per capsule. Larger unit dosages, such as 15, 20 or 25 mg, can be prepared by using 15, 20 or 25 grams glaucine phosphate and lactose q.s. to 300 grams. Smaller dosages are similarly prepared, using l-glaucine tosylate, l-glaucine-d-tartrate, d,l-glaucine sulfate or a 1:1 mixture of l-glaucine salicylate and d,l-glaucine citrate.

EXAMPLE 11

In other operations, various dosages of d,l-glaucine phosphate were administered to groups of mice by the oral route or by intraperitoneal injection, and the dosage which is lethal to 50 percent of the mice ($LD_{50}$) was calculated from the mortality observations within 72 hours after administration. The $LD_{50}$ for intraperitoneal injection was found to be 178 mg/kg. The oral $LD_{50}$ is these operations was found to be equal to or greater than 681 mg/kg. The oral and intraperitoneal $LD_{50}$'s for d,l-glaucine lactate were similarly found to be 383 mg/kg (oral) and 178 mg/kg (i.p.).

What is claimed is:

1. A method of alleviating pain in animals, comprising administering to an animal an analgesic amount of a pharmaceutically-acceptable salt of a glaucine compound selected from the group consisting of l-glaucine, d,l-glaucine and a mixture thereof.

2. Method of claim 1 wherein the compound is a d,l-glaucine phosphate.

3. Method of claim 1 wherein the compound corresponds to d,l-glaucine phosphate having the molecular formula $C_{21}H_{25}NO_4 \cdot 1\frac{1}{2} H_3PO_4$.

4. Method of claim 1 wherein the compound is l-glaucine phosphate.

5. Method of claim 1 wherein the compound is d,l-glaucine hydrobromide.

6. Method of claim 1 wherein the compound is d,l-glaucine lactate.

7. Method of claim 1 wherein the compound is administered orally.

8. Method of claim 1 wherein the pharmaceutically-acceptable salt is selected from the group consisting of the hydrobromide, phosphate, lactate, acetate, pamoate, tosylate, citrate, sulfate, maleate and salicylate salts.

9. A method of alleviating pain in animals, comprising administering to an animal an analgesic amount of a glaucine compound selected from the group consisting of l-glaucine and a mixture thereof with racemic d,l-glaucine, and a pharmaceutically-acceptable salt thereof.

* * * * *

UNITED STATES PATENT AND TRADEMARK OFFICE
CERTIFICATE OF CORRECTION

PATENT NO. : 4,183,939    Page 1 of 2
DATED : January 15, 1980
INVENTOR(S) : Thomas H. Gieske, et al.

It is certified that error appears in the above-identified patent and that said Letters Patent are hereby corrected as shown below:

Column 2, between lines 1-10, formula should read

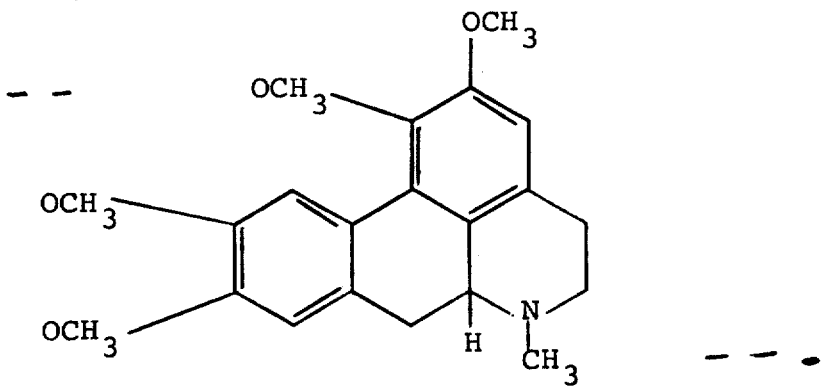

Column 2, line 19, "addication," should read --addiction,--.

Column 3, line 27, "in" should read --is--.

Column 3, line 63, "table" should read --tablet--.

Column 4, line 52, "(2:3 salts)" should read --(2:3 salt)--.

Column 5, line 27, "and $ED_{50}$" should read --an $ED_{50}$--.

UNITED STATES PATENT AND TRADEMARK OFFICE
CERTIFICATE OF CORRECTION

PATENT NO. : 4,183,939

DATED : January 15, 1980

INVENTOR(S) : Thomas H. Gieske, et al.

It is certified that error appears in the above–identified patent and that said Letters Patent are hereby corrected as shown below:

Column 5, line 51, "The" should read --In--.

Column 5, line 68, "minutes" should read --minute--.

Column 8, line 1, "is" should read --in--.

Signed and Sealed this

Third Day of June 1980

[SEAL]

Attest:

SIDNEY A. DIAMOND

Attesting Officer

Commissioner of Patents and Trademarks